(12) United States Patent
Sumida et al.

(10) Patent No.: US 7,925,070 B2
(45) Date of Patent: Apr. 12, 2011

(54) METHOD FOR DISPLAYING VIRTUAL SLIDE AND TERMINAL DEVICE FOR DISPLAYING VIRTUAL SLIDE

(75) Inventors: Youichi Sumida, Kobe (JP); Takuma Watanabe, Kobe (JP); Ryuichiro Emi, Kakogawa (JP); Toshio Kawaguchi, Chikushino (JP); Kiyoaki Watanabe, Tokyo (JP); Yohko Kawai, Tokyo (JP); Takayuki Mitsuhashi, Sagamihara (JP)

(73) Assignee: Sysmex Corporation, Kobe (JP)

( * ) Notice: Subject to any disclaimer, the term of this patent is extended or adjusted under 35 U.S.C. 154(b) by 961 days.

(21) Appl. No.: 11/094,053

(22) Filed: Mar. 30, 2005

(65) Prior Publication Data
US 2006/0050948 A1 Mar. 9, 2006

(30) Foreign Application Priority Data

Mar. 30, 2004 (JP) ................. 2004-098603
Mar. 30, 2004 (JP) ................. 2004-099641

(51) Int. Cl.
*G06K 9/00* (2006.01)
(52) U.S. Cl. ........................................ 382/134
(58) Field of Classification Search .................. None
See application file for complete search history.

(56) References Cited

U.S. PATENT DOCUMENTS

| | | | |
|---|---|---|---|
| 5,016,283 A | 5/1991 | Bacus et al. | |
| 5,107,422 A * | 4/1992 | Kamentsky et al. | 382/133 |
| 6,031,930 A | 2/2000 | Bacus et al. | |
| 6,101,265 A | 8/2000 | Bacus et al. | |
| 6,226,392 B1 | 5/2001 | Bacus et al. | |
| 6,272,235 B1 * | 8/2001 | Bacus et al. | 382/133 |
| 6,396,941 B1 | 5/2002 | Bacus et al. | |
| 6,404,906 B2 | 6/2002 | Bacus et al. | |
| 6,466,690 B2 | 10/2002 | Bacus et al. | |
| 6,522,774 B1 | 2/2003 | Bacus et al. | |
| 2002/0001402 A1 * | 1/2002 | Berliner | 382/133 |
| 2002/0118389 A1 | 8/2002 | Fukuda et al. | |
| 2004/0170312 A1 * | 9/2004 | Soenksen | 382/133 |

FOREIGN PATENT DOCUMENTS

| | | |
|---|---|---|
| JP | 63-231263 | 9/1988 |
| JP | 01-165958 A | 6/1989 |
| JP | 05-249102 | 9/1993 |
| JP | 11-083848 | 3/1999 |
| JP | 2001-211875 | 8/2001 |
| JP | 2001-231760 | 8/2001 |
| JP | 2002-117040 | 4/2002 |
| JP | 2004-046325 | 2/2004 |
| WO | WO 98/39728 A1 | 9/1998 |
| WO | WO 98/44446 A1 | 10/1998 |
| WO | WO 03/073365 A1 | 9/2003 |
| WO | WO 03/096228 A1 | 11/2003 |

* cited by examiner

*Primary Examiner* — Vu Le
*Assistant Examiner* — Claire Wang
(74) *Attorney, Agent, or Firm* — Brinks Hofer Gilson & Lione

(57) ABSTRACT

The invention relates to a method for displaying a virtual slide capable of storing positional information of a prescribed cell in a virtual slide photographed with a magnification capable of recognizing cell morphology and a terminal device for displaying the virtual slide; or a method for displaying the virtual slide capable of classifying the prescribed cell in the virtual slide photographed with a magnification capable of recognizing cell morphology by a simple operation; or a terminal device for displaying the virtual slide.

12 Claims, 15 Drawing Sheets

| No. | LARGE CLASSIFICATION | SMALL CLASSIFICATION |
|---|---|---|
| 1 | Class 1 (MARROW TYPE) | Blast (blast cell) |
| 2 | | Promyelo (promyelocyte) |
| 3 | | Myelo (myelocyte) |
| 4 | | Meta (metamyelocyte) |
| 5 | | Band (band cell) |
| 6 | | Seg (segmented leukocyte) |
| 7 | Class 2 (WHITE BLOOD CELLS OTHER THAN MARROW TYPE) | Eosino (eocinophile leukocyte) |
| 8 | | Baso (basocyte) |
| 9 | | Lymph (lymphocyte) |
| 10 | | A.lymph (abnormal lymphocyte) |
| 11 | | Mono (monocyte) |
| 12 | Class 3 (EBL TYPE) | EBL-Pro (proerythroblast) |
| 13 | | EBL-Baso (basophilic erythroblast) |
| 14 | | EBL-Poly (polychromatic erythroblast) |
| 15 | | EBL-Orth(orthochromatic erythroblast) |
| 16 | Class 4 (OTHER WHITE BLOOD CELLS) | Plasma (plasma cell) |
| 17 | | Reticulum (reticular cell) |
| 18 | | Mast (mast cell) |
| 19 | | Mitosis (mitosis cell) |
| 20 | | Other (other cells) |

VIRTUAL SLIDE DIVISION FLOW

CLASSIFICATION COUNT FLOW

FIG. 12

| No. | LARGE CLASSIFICATION | SMALL CLASSIFICATION |
|---|---|---|
| 1 | Class 1 (MARROW TYPE) | Blast (blast cell) |
| 2 | | Promyelo (promyelocyte) |
| 3 | | Myelo (myelocyte) |
| 4 | | Meta (metamyelocyte) |
| 5 | | Band (band cell) |
| 6 | | Seg (segmented leukocyte) |
| 7 | Class 2 (WHITE BLOOD CELLS OTHER THAN MARROW TYPE) | Eosino (eocinophile leukocyte) |
| 8 | | Baso (basocyte) |
| 9 | | Lymph (lymphocyte) |
| 10 | | A.lymph (abnormal lymphocyte) |
| 11 | | Mono (monocyte) |
| 12 | Class 3 (EBL TYPE) | EBL-Pro (proerythroblast) |
| 13 | | EBL-Baso (basophilic erythroblast) |
| 14 | | EBL-Poly (polychromatic erythroblast) |
| 15 | | EBL-Orth (orthochromatic erythroblast) |
| 16 | Class 4 (OTHER WHITE BLOOD CELLS) | Plasma (plasma cell) |
| 17 | | Reticulum (reticular cell) |
| 18 | | Mast (mast cell) |
| 19 | | Mitosis (mitosis cell) |
| 20 | | Other (other cells) |

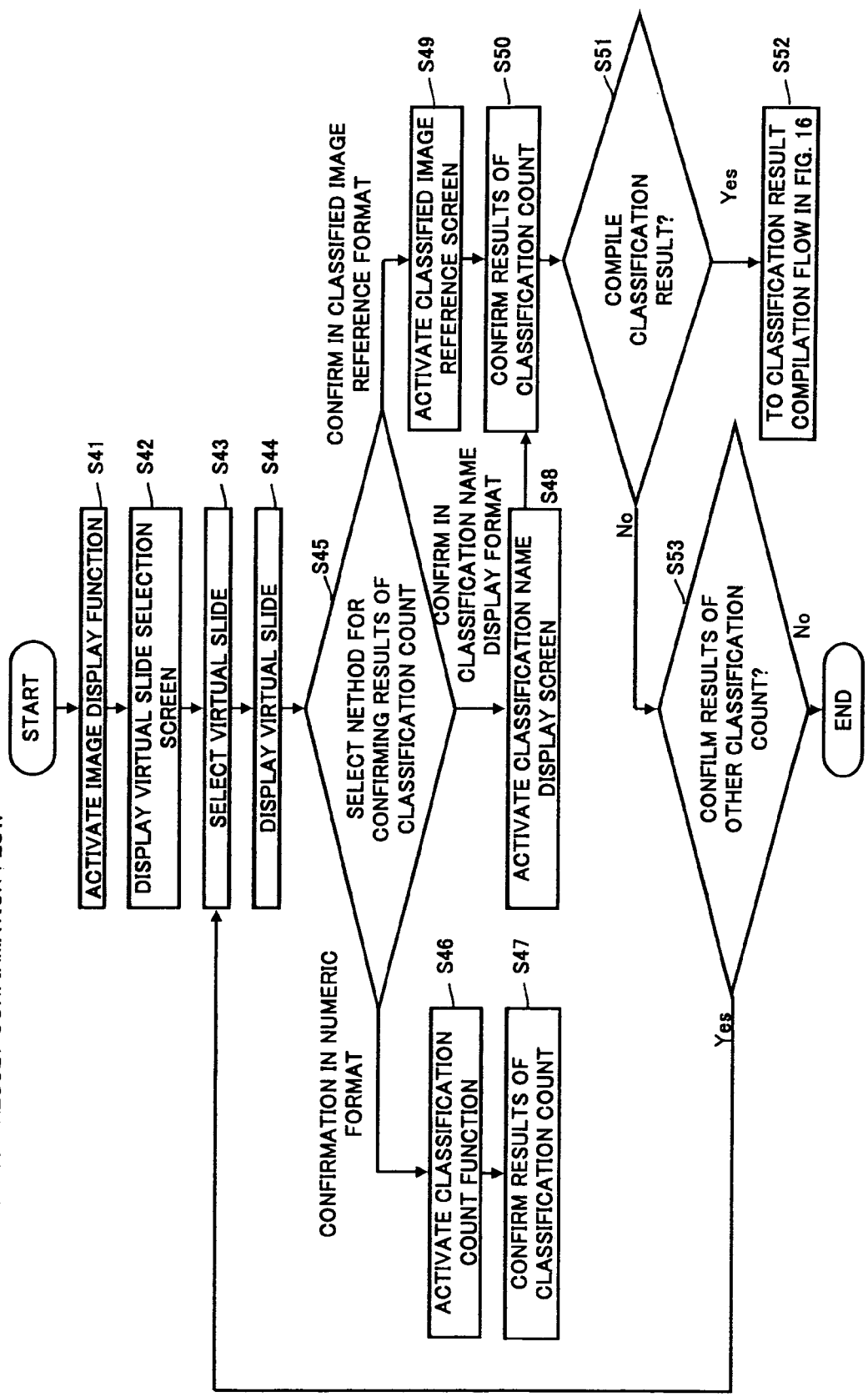

CLASSIFICATION RESULT COMPILATION FLOW

```
START
  ↓
CORRECT CLASSIFICATION RESULT ── S61
  ↓
CORRECTION OF CLASSIFICATION RESULT HAS BEEN COMPLETED? ── S62
  No → (loop back)
  Yes ↓
UPLOAD CLASSIFICATION RESULTS TO SERVER, AND REGISTER TO DATABASE ── S63
  ↓
END
```

METHOD FOR DISPLAYING VIRTUAL SLIDE AND TERMINAL DEVICE FOR DISPLAYING VIRTUAL SLIDE

This application claims priority under 35 U.S.C. §119 to Japanese Patent Application Nos. 2004-98603 and 2004-99641 both filed Mar. 30, 2004, the entire contents of which are hereby incorporated herein by reference.

BACKGROUND OF THE INVENTION

1. Field of the Invention

The invention relates to a method for displaying a virtual slide photographed with a magnification capable of recognizing cell morphology, and a terminal device for displaying the virtual slide.

2. Background Art

In conventional blood cell examination, a method referred to "microscopic inspection" has been employed for visual observation under the microscope of a smear sample prepared by spreading blood as an inspection object on a slide glass. In this microscopic inspection, the smear sample is observed under a microscope and, for example, white blood cells found in a given area are subjected to classification count using an exclusive use classification counter in which classification items of the blood cells are allotted to each key. When abnormally shaped erythrocytes and platelets, or cells that are difficult to decide their classification items are found during the classification count work, the cells are photographed with a video camera mounted on the microscope. The images of the photographed blood cells are stored in a database of an image filing system together with attribute information such as medical record card numbers. The results of the classification counts as well as the stored images of the blood cells, if necessary, are printed out after the examination has been completed to obtain inspection results.

In the above-mentioned method, however, since the smear sample is visually inspected under a microscope, the examiner is required to examine the sample in a room where the microscope is provided. Accordingly, the examiner's work is disadvantageously restricted in a specified room.

An art for preparing a virtual microscopic slide after taking a photograph using microscope for pathological cytodiagnosis has been proposed in WO98/39728. Since the virtual microscopic slide can be delivered through an internet according to WO98/39728, it is possible to observe the virtual microscopic slide using a computer in which a prescribed program has been installed. Since the inspector's work is not restricted in a room where the microscope is provided by using the art described in the patent document described above, examinations are possible using the virtual microscope slide without any restriction of the room.

However, descriptions on neither the virtual microscope slide of blood sample nor conducting the classification count of the blood cells using the virtual microscope slide, as well no description of filing of the examined blood cell images, are found in WO98/39728. Also, WO98/39728 does not describe an art for retrieving the blood cells corresponding to the filed blood cell image from the virtual microscope slide. In the examination of the blood cells using the virtual microscope slide of the blood sample, a supervisor is required to re-classify after the examination when blood cells that are difficult to classify in the preceding examination emerges. Therefore, many blood cell images should be stored in the virtual microscope slide. When the classification items of the stored blood cell images are re-discriminated, information of cell images around the cell images to be examined, not only observing the cell's own images, are often required. However, the work for re-classification becomes complicated, when the corresponding cells are visually searched again from the virtual microscope slide and information around the cells and the like are confirmed.

SUMMARY OF THE INVENTION

An object of the invention is to provide a method for displaying the virtual slide capable of facilitating the work for re-judging the cell images, and a terminal device for displaying the virtual slide.

Another object of the invention is to provide a method for efficient classification count work using the virtual slide, and a terminal device for displaying the virtual slide.

A first aspect of the invention relates to a method comprising the steps of: displaying an image display part for displaying the virtual slide photographed with a magnification capable of recognizing cell morphology and a pointer for specifying a position of a cell displayed on the image display part; and storing at least positional information of the desired cell in the sample image based on storage instruction.

A second aspect of the invention relates to a terminal device for displaying a virtual slide comprising: a display; a virtual slide display means for displaying a virtual slide display means for displaying a virtual slide photographed with a magnification capable of recognizing cell morphology on a image display part of a screen displayed on the display; a position specification means for specifying a position of a cell in the virtual slide; a storage instruction means for instructing storage of positional information of the cell specified by the position specification means; and a storage means for storing positional information of the cell specified by the position specification means based on storage instruction by the storage instruction means.

A third aspect of the invention relates to method for displaying a virtual slide comprising the steps of: displaying an image display part for displaying the virtual slide photographed with a magnification capable of recognizing cell morphology; displaying a classification count display part for displaying count numbers for every classification items of the cell; displaying a pop-up menu including the plural classification items of the cell on the image display part; selecting the classification items corresponding to a specified cell in the sample image displayed on the image display part from the pop-up menu; and counting the classification item selected for the prescribed cell while displaying a total count number of the counted classification items on the classification count display part.

A fourth aspect of the present invention relates to a terminal device for displaying a virtual slide comprising: a first display means for displaying an image display part for displaying the virtual slide photographed with a magnification capable of recognizing cell morphology; a second display means for displaying a classification count display part for displaying count numbers for every classification items of a cell; a specification means for specifying the cell in the virtual slide displayed on the image display part; a menu display means for displaying a pop-up menu including the plural classification items on the image display part upon specification by the specification means; a selection means for selecting the classification items corresponding to the specified cell from the pop-up menu; and a classification count means for counting the selected classification items and for displaying a total count number of the counted classification items on the classification count display part.

BRIEF DESCRIPTION OF THE DRAWINGS

FIG. 12 is provided for describing classification count items for classification count of the white blood cells according to an embodiment of the invention;

FIG. 13 shows a flow chart for describing a confirmation action of the results of classification according to an embodiment of the invention;

DESCRIPTION OF THE PREFERRED EMBODIMENTS

Figure 1:
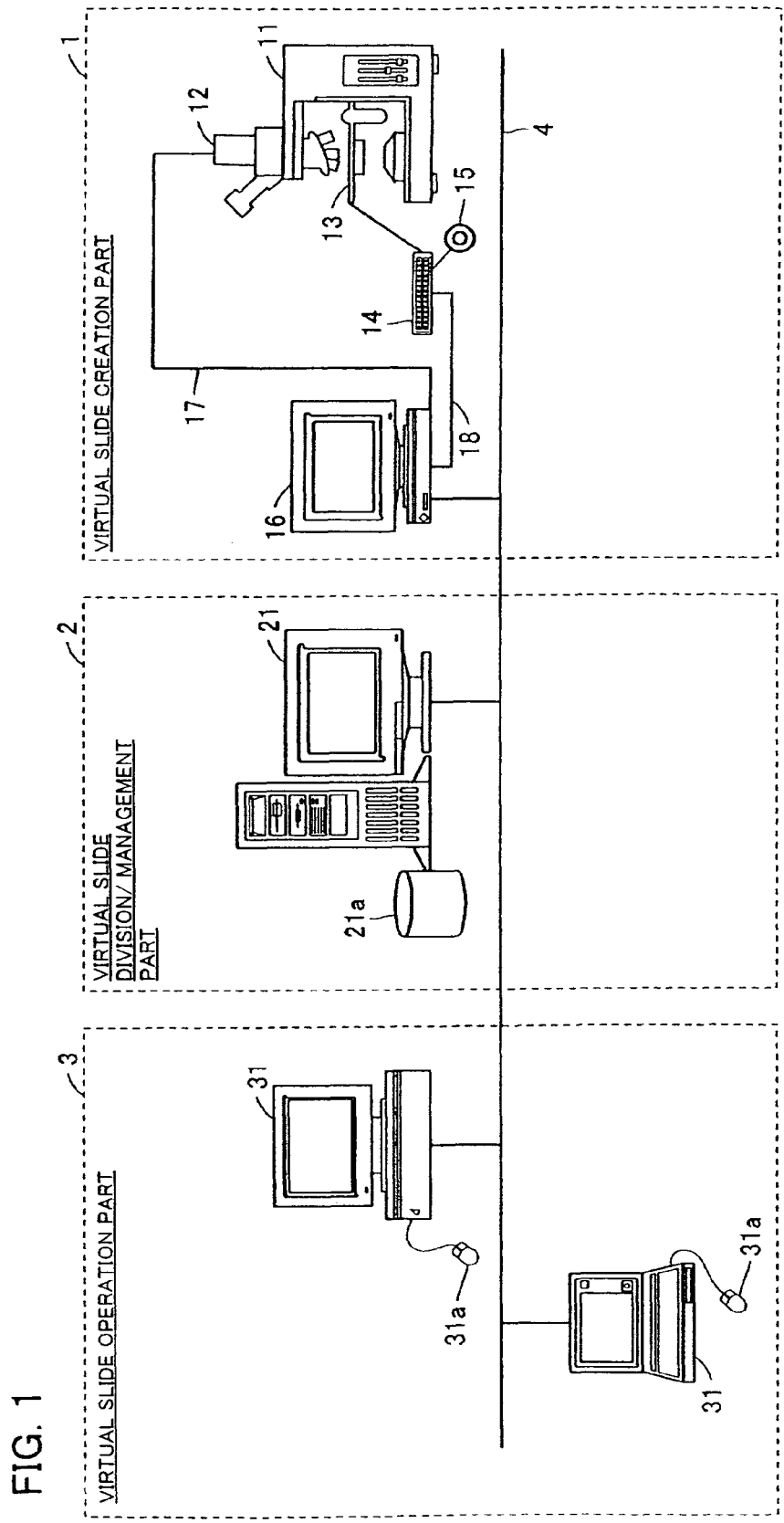
FIG. 1 illustrates an overall construction of the system for embodying the method for displaying a virtual slide (blood cell image) according to an embodiment of the invention.

FIG. 1 shows an overall system construction for practical application of the display method of the virtual microscope slide (blood cell image) according to an embodiment of the invention.

The system for practically applying the virtual slide display method according to this embodiment is composed of a virtual slide creation part 1, a virtual slide division and management part 2, and a virtual slide operation part 3 as shown in FIG. 1. The virtual slide creation part 1 comprises an optical microscope 11 for confirming the sample slide having magnifications of 20 and 100; a 3CCD camera 12 for incorporating images; an automatic stage 13 for positional control of the optical microscope 11 in X, Y and Z directions; a control unit 14 and a joystick 15 for controlling the automatic stage 13; and an automatic stage control terminal 16 for controlling the automatic stage 13 as well as for focus synthesis and image tiling. The optical microscope 11 used is, for example, a BX-50 series microscope manufactured by Olympus Corporation, and the automatic stage 13 used is, for example, H101BX manufactured by PRIOR. The 3CCD camera 12 used is, for example, KY-F70B manufactured by Victor Company of Japan, Limited. The automatic stage control terminal 16 is connected to the 3CCD camera 12 through an image signal transfer cable 17 while it is connected to the control unit 14 through a control unit control cable 18. The automatic stage control terminal 16 is connected to a LAN cable 4 as a network cable.

The virtual slide division and management part 2 comprises a server 21 for managing virtual slide data and for dividing images. The server 21 includes a database 21a for storing the virtual slide data and data of results of classification count. The server 21 is connected to the LAN cable 4 as the network cable. Each virtual slide data is stored in the database 21a together with a line of discrimination information such as a sample number. A table correlating a line of discrimination information and attribute information is also stored in the database 21a. Attribute information comprises patient attribute information such as patient number, patient name, distinction of sex, age, blood type, ward, examination division, disease name, clinical history, physician in charge and examination results, as well as sample attribute information such as blood examination date, request number, sampling date, classification of the sample and comment on the sample. The data of the results of classification count to be stored in the database 21a of the server 21 include cell images of the cells subjected to classification count, positional information of the cells, classification names, classification date and the name of a person in charge of classification. The virtual slide operation part 3 comprises a client terminal 31 for classification count using the virtual slide. A mouse 31a is provided in the client terminal 31. The client terminal 31 is connected to the LAN cable 4 as the network cable.

Figure 2:
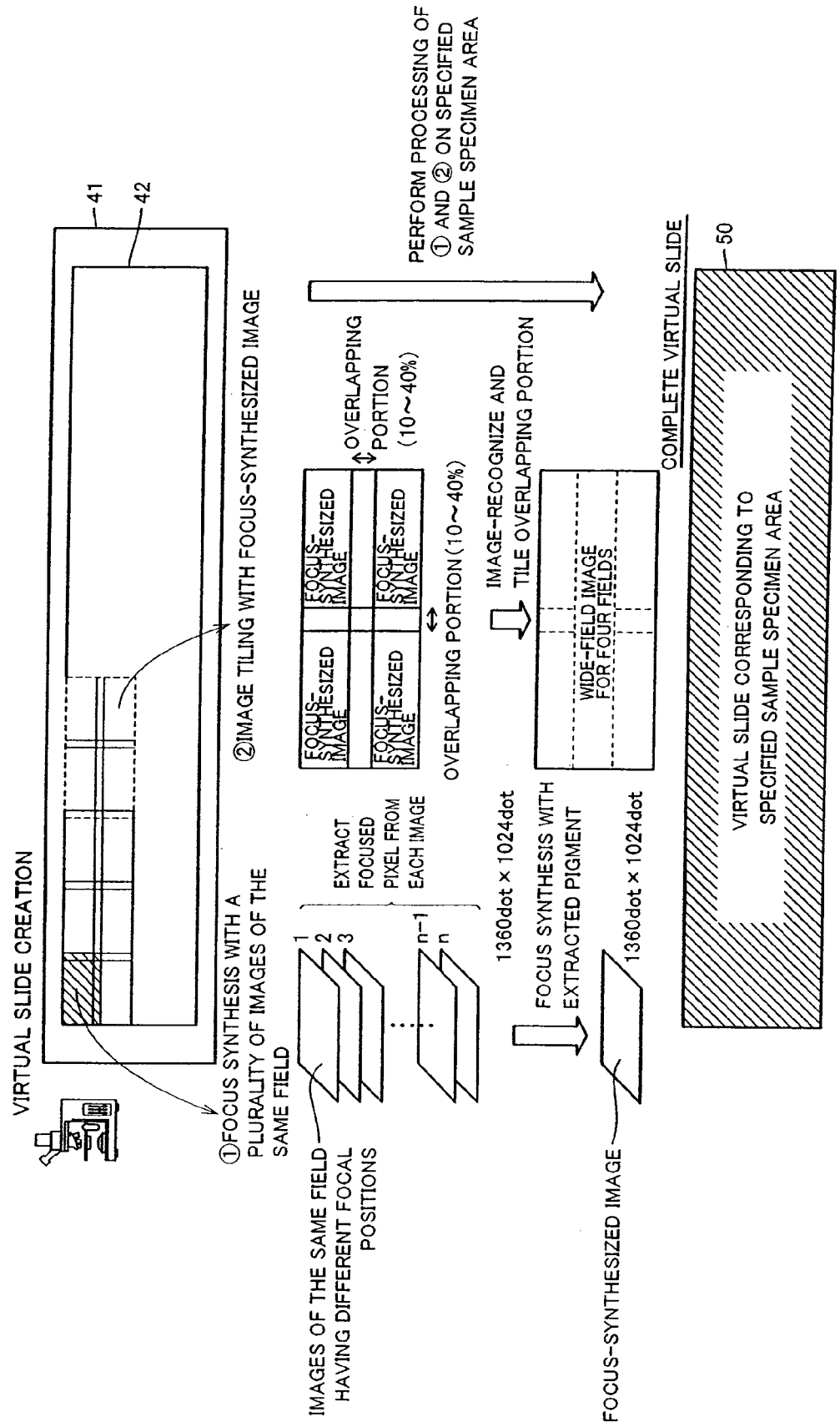
FIG. 2 is a diagram illustrating a method for preparing a virtual slide according to an embodiment of the invention.
Figure 3:
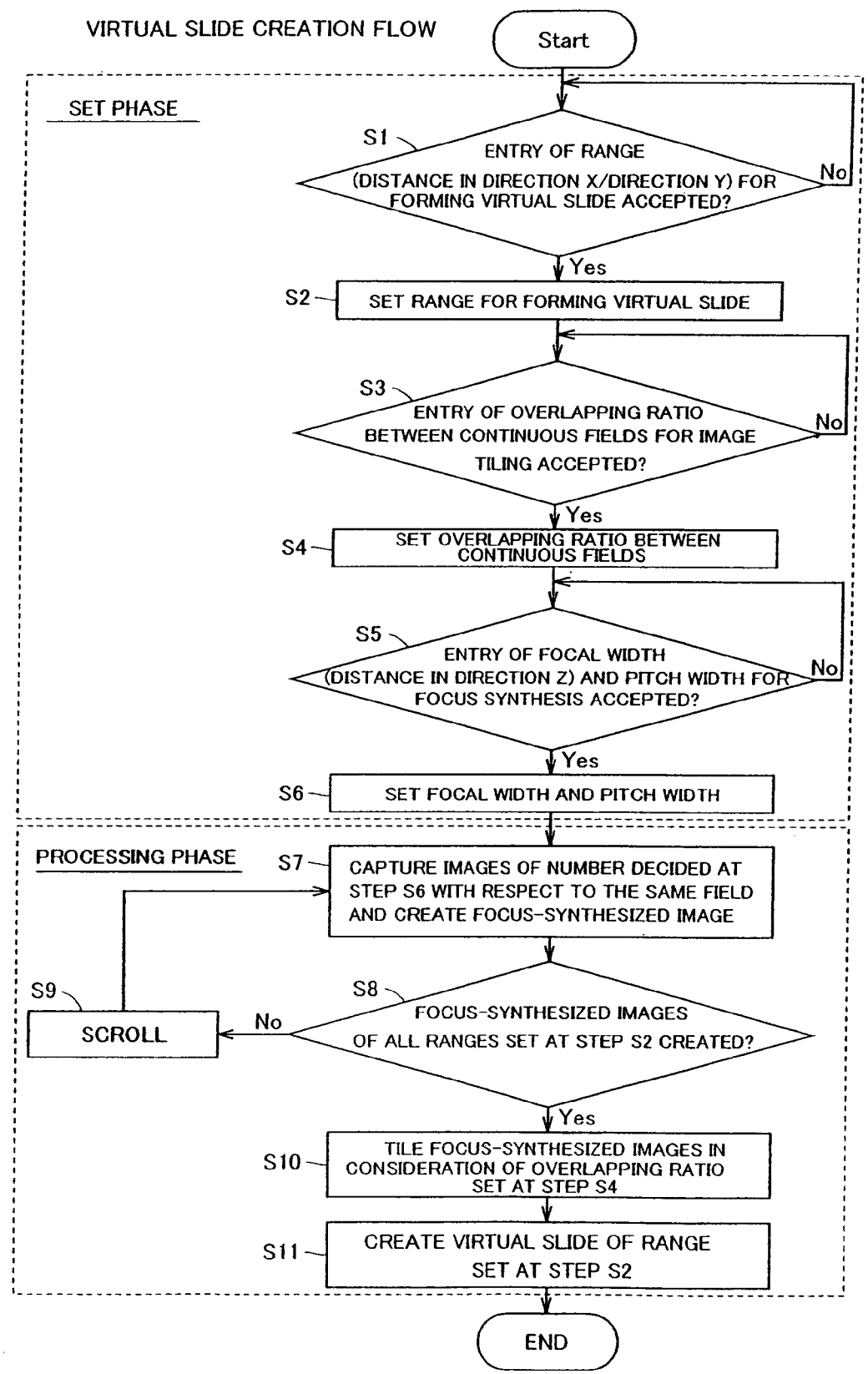
FIG. 3 shows a flow chart for illustrating a flow for preparing a virtual slide according to an embodiment of the invention.

FIG. 2 is a diagram illustrating a method for preparing a virtual slide, and FIG. 3 shows a flow chart for illustrating a flow for preparing a virtual slide. The method for preparing the virtual slide will be described below with reference to FIGS. 1 to 3. The virtual slide is prepared at the virtual slide creation part 1 shown in FIG. 1. The flow for preparing the virtual slide is composed of a setting phase and a processing phase as shown in FIG. 3. In the setting phase, an operator places a sample on the automatic stage 13 of the optical microscope 11 (see FIG. 1). Then, whether input of a range for preparing the virtual slide (the distances in the X and Y direction of the test sample area) has been accepted or not is judged by the automatic stage control terminal 16 in step S1 shown in FIG. 3. When input of the range for preparing the virtual slide is judged not to have been accepted in step S1, the operator inputs the range for preparing the virtual slide using an input unit of the automatic stage control terminal 16. When the range for preparing the virtual slide is inputted, the range for preparing the virtual slide is set in the automatic stage control terminal 16 in step S2. Whether input of an overlap ratio of continuous fields of vision for image tiling has been accepted or not is judged thereafter by the automatic stage control terminal 16 in step S3. When input of the overlap ratio is judged not to have been accepted in step S3, the operator inputs the overlap ratio using an input unit of the automatic stage control terminal 16. When the overlap ratio has been inputted, the overlap ratio is set in the automatic stage control terminal 16 in step S4. The overlap ratio is preferably determined to be about 10% or more and 40% or less. Then, whether input of a focus width (the distance in the Z direction)

for focus synthesis and a notch width has been accepted or not is judged by the automatic stage control terminal 16 in step S5. When input of the focus width and the notch width is judged not to have been accepted in step S5, the operator inputs the focus width and the notch width using the input unit of the automatic stage control terminal 16. When the focus width and the notch width are inputted, they are set in the automatic stage control terminal 16 in step S6. The number of images incorporated into the same field of vision is determined by setting the focus width and the notch width. In this embodiment, the focus width is set to be about 1 mm or less while the notch width is set to be about 1 μm. The setting phase of the virtual slide preparation flow is completed by the processing from step S1 through step S6 described above.

In the processing phase, in step S7, the images corresponding to the number of images in the same field of vision determined in step S6 are incorporated into the automatic stage control terminal 16 through the 3CCD camera 12, and a focus synthesis image is formed in the automatic stage control terminal 16. The term "focus synthesis" as used herein refers to a processing for forming one image into a totally sharp focus by extracting focused images from the images having different focuses in the same field of vision. A focus synthesis image with a resolution of 1,360 dots×1,024 dots as shown in FIG. 2 is formed by applying this focus synthesis to the images in the incorporated entire field of vision in this embodiment. A TIF format is used as an image format of the focus synthesis image. Whether the focus synthesis image has been formed or not in the entire range set in step S2 is judged thereafter in step S8 shown in FIG. 3. When judged not to have been formed, the field of vision is displaced in step S9, and the focus synthesis in step S7 is applied again. This processing is repeated until the focus synthesis image is formed in the entire range set in step S2.

When the focus synthesis image is judged to have been formed in the entire range in step S8, the focus synthesis images are tiled with each other as shown in FIG. 2 using the automatic stage control terminal 16 in step S10 by taking the overlap ratio determined in step S4 into consideration. The individual synthesis images are tiled so that joints between them are not evident by image recognition of overlap portions of the adjoining focus synthesis images when the images are tiled. In step S11, the images are tiled in the entire range determined in step S2 to complete the virtual slide 50 as shown in FIG. 2. The image format used for the virtual slide 50 is an BMP format. The virtual slide 50 prepared in step S9 has a size of about 220,000 dots×134,000 dots. The virtual slide 50 prepared using the automatic stage control terminal 16 is stored in the server 21 through the LAN cable 4.

Figure 4:
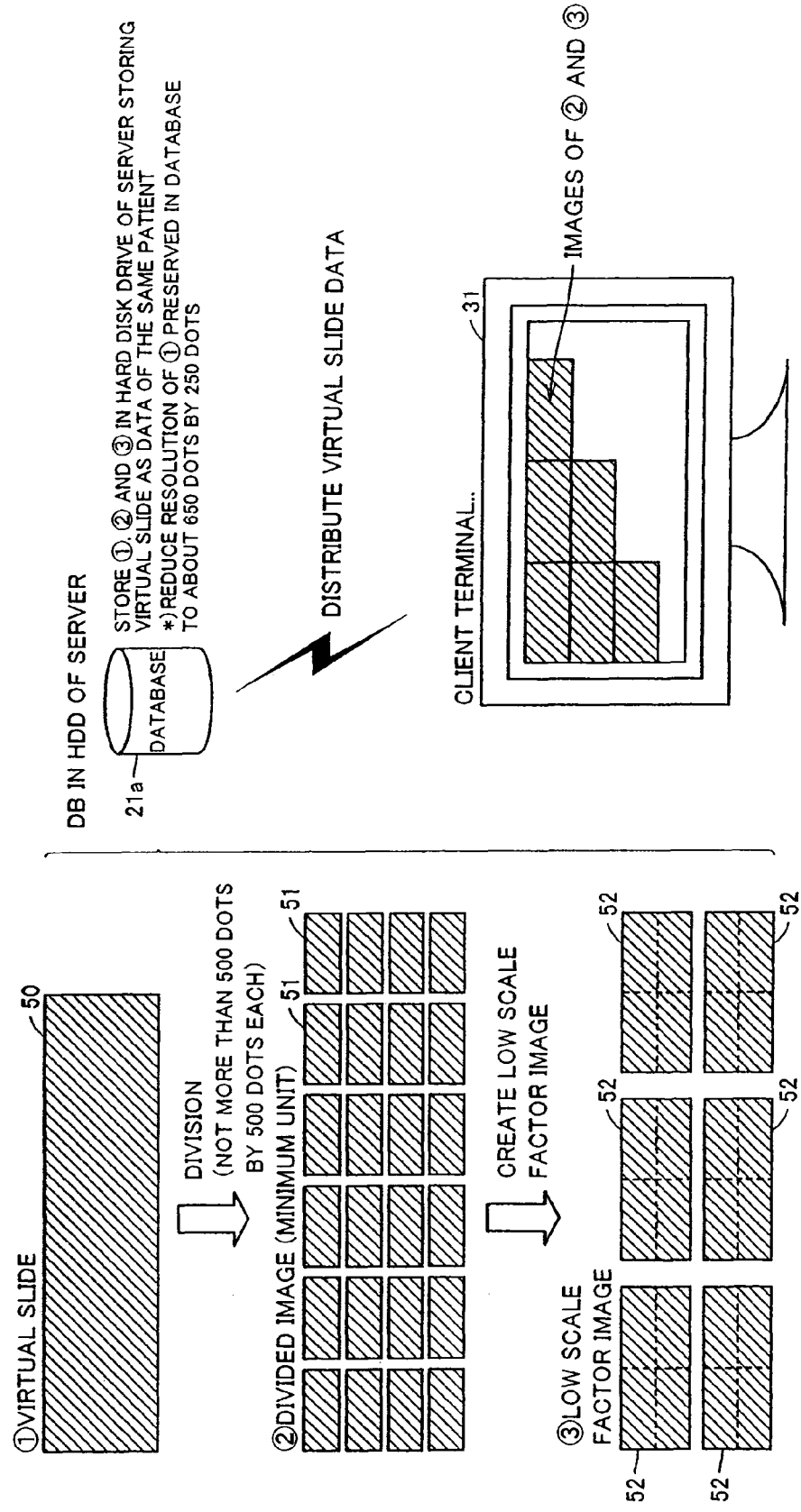
FIG. 4 schematically illustrates a method for dividing and managing a virtual slide according to an embodiment of the invention.
Figure 5:
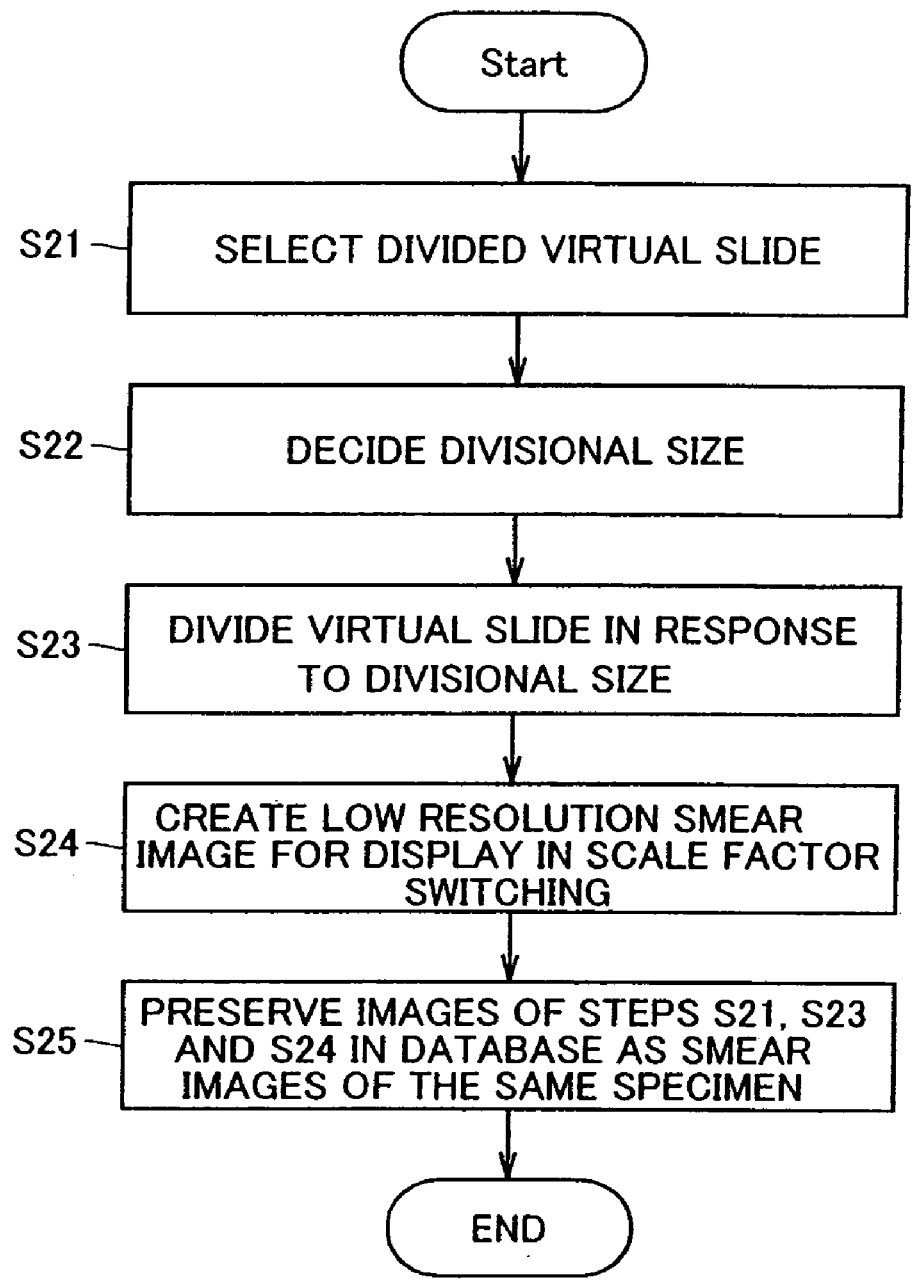
FIG. 5 shows a flow chart for illustrating a division flow of a virtual slide according to an embodiment of the invention.

FIG. 4 schematically illustrates a method for dividing and managing the virtual slide, while FIG. 5 shows a flow chart for illustrating a division flow of the virtual slide. Division and management of the virtual slide is implemented in the server 21 of the virtual slide division and management part 2 shown in FIG. 1. For dividing the virtual slide, a virtual slide 50 to be divided is selected from the virtual slides 50 stored in the server 21 and having a size of about 220,000 dots×134,000 dots (see FIG. 4) in step S21 shown in FIG. 5. The division size is determined in step S22. In this embodiment, the virtual slide is divided into a size of 500 dots×500 dots per one slide as shown in FIG. 4. The division size is preferably from 500 dots×500 dots through 1,300 dots×1,300 dots when the image resolution of the client terminal 31 is SXGA (1280×1024). The division size is determined as a whole depending on the image resolution of the client terminal 31, specification of the terminal, and communication line speed. The divided image 51 as shown in FIG. 4 is formed by dividing the virtual slide 50 in step S23 in accordance with the division size determined in step S12. The image format used for divided image 51 is a JPEG format (Photoshop Version 7.0.1 with a compression ratio of about 10).

A low magnification image 52 (see FIG. 4) is prepared in step S24. Specifically, a wide view field image (low magnification image 52) is prepared by joining several images (four images in this embodiment) of respective divided images 51 as shown in FIG. 4. The file size is reduced by diminishing image resolution of the wide view field images (low magnification image 52) prepared. For example, low magnification images 52 with magnifications of 60, 40, 20 and 10 are formed from the divided image 51 of the virtual slide 50 formed by using an objective lens of the optical microscope 11 with a magnification of 100 (see FIG. 1) for forming the low magnification image 52. The low magnification image 52 is an example of the "partial image" of the invention. The image format used for the low magnification image 52 is the JPEG format (Photoshop Version 7.0.1 with a compression ratio of about 10).

In step S25, the virtual slide 50 as the total image prepared in steps S21, S23 and S24, and the divided image 51 and low magnification image 52 as partial images are stored in the database 21$a$ in the server 21 shown in FIG. 1 as sample images of one test object (the same patient) together with their discrimination information. In this case, resolution of the virtual slide 50 as a total image to be stored in the database 21$a$ is reduced to a size of about 650 dots×250 dots. A relational database is used for the database 21$a$ in the server 21 in which the virtual slide 50, the divided image 51 and low magnification image 52 are accumulated.

Figure 6:
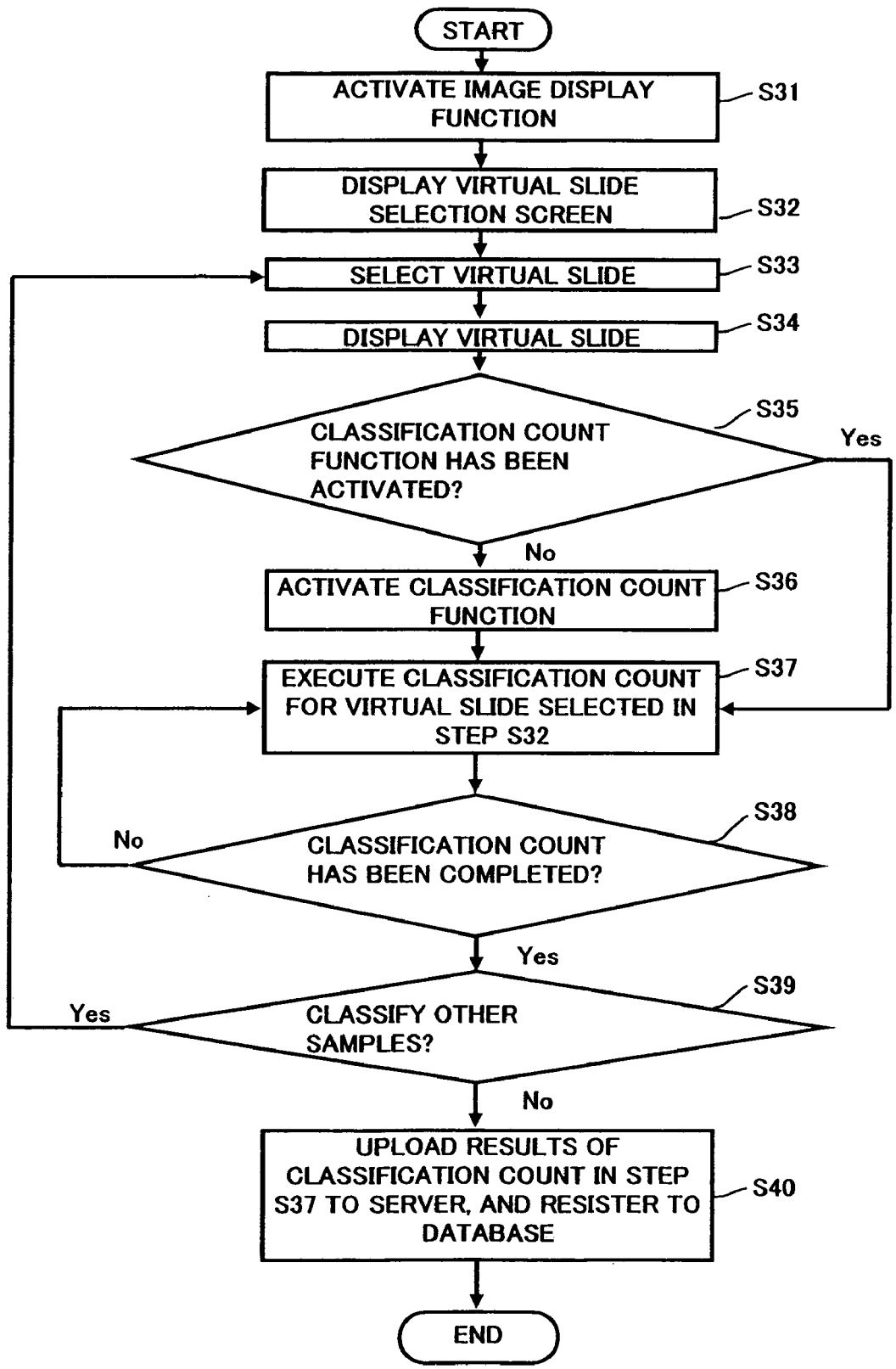
FIG. 6 shows a flow chart for illustrating a classification count action of the white blood cells according to an embodiment of the invention.

FIG. 6 shows a flow chart for illustrating a classification count action of the white blood cells using the virtual slide. FIGS. 7 to 11 show screens displayed in the client terminal when the white blood cells are classified and counted. FIG. 12 is provided for describing classification count items for classification count of the white blood cells. The classification count action of the white blood cells using the virtual slide according to this embodiment will be described below with reference to FIGS. 1 to 4 and FIGS. 6 to 12. The white blood cells are subjected to classification count at the client terminal 31. For displaying partial images of the virtual slide to be described below on the client terminal 31, a recording medium such as FD and CD in which a program for implementing the display method of the virtual slide according to this embodiment should be integrated into the client terminal 31, or a program should be installed from the recording medium into the client terminal 31.

Figure 7:
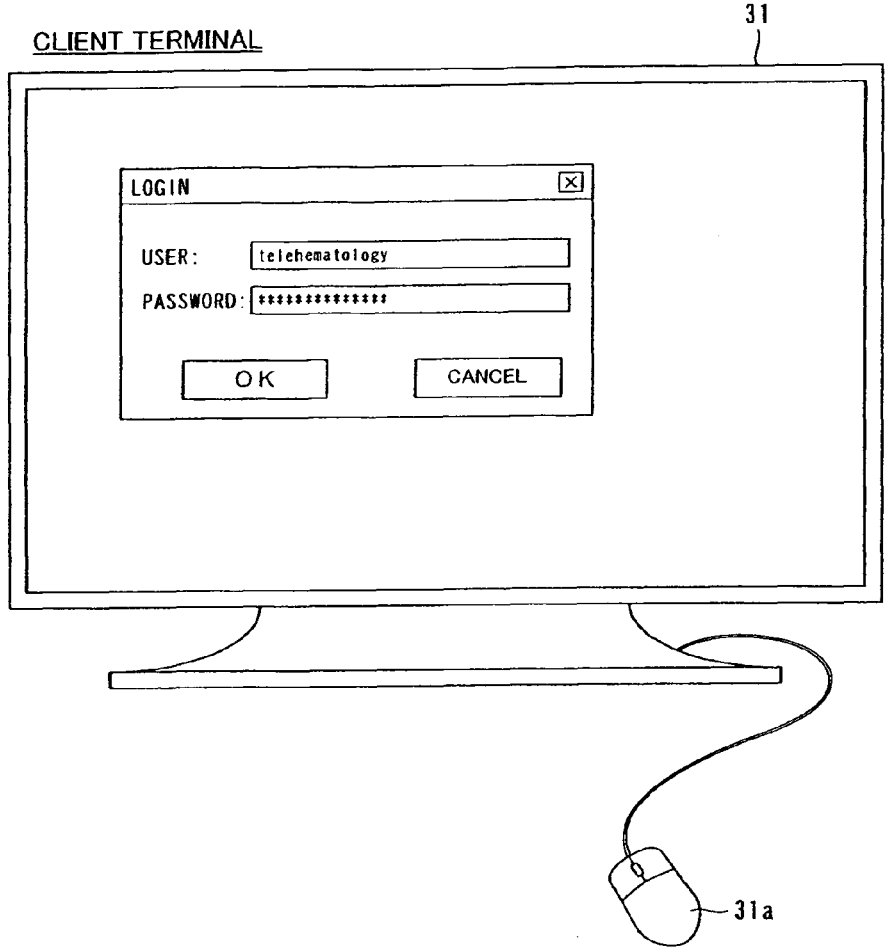
FIG. 7 shows an input screen for a user ID and password for activating an image display function according to an embodiment of the invention.
Figure 8:
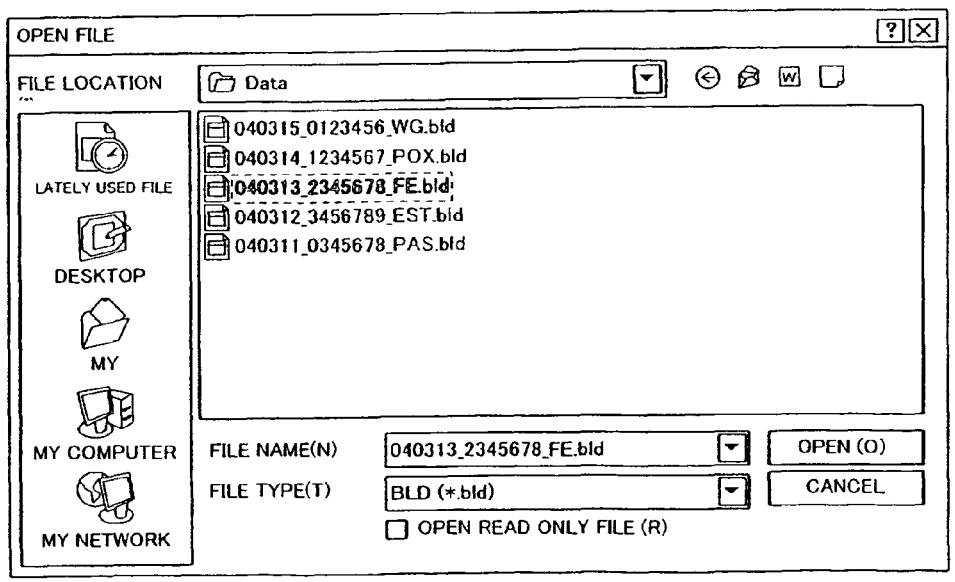
FIG. 8 shows a virtual slide selection screen according to an embodiment of the invention.
Figure 9:
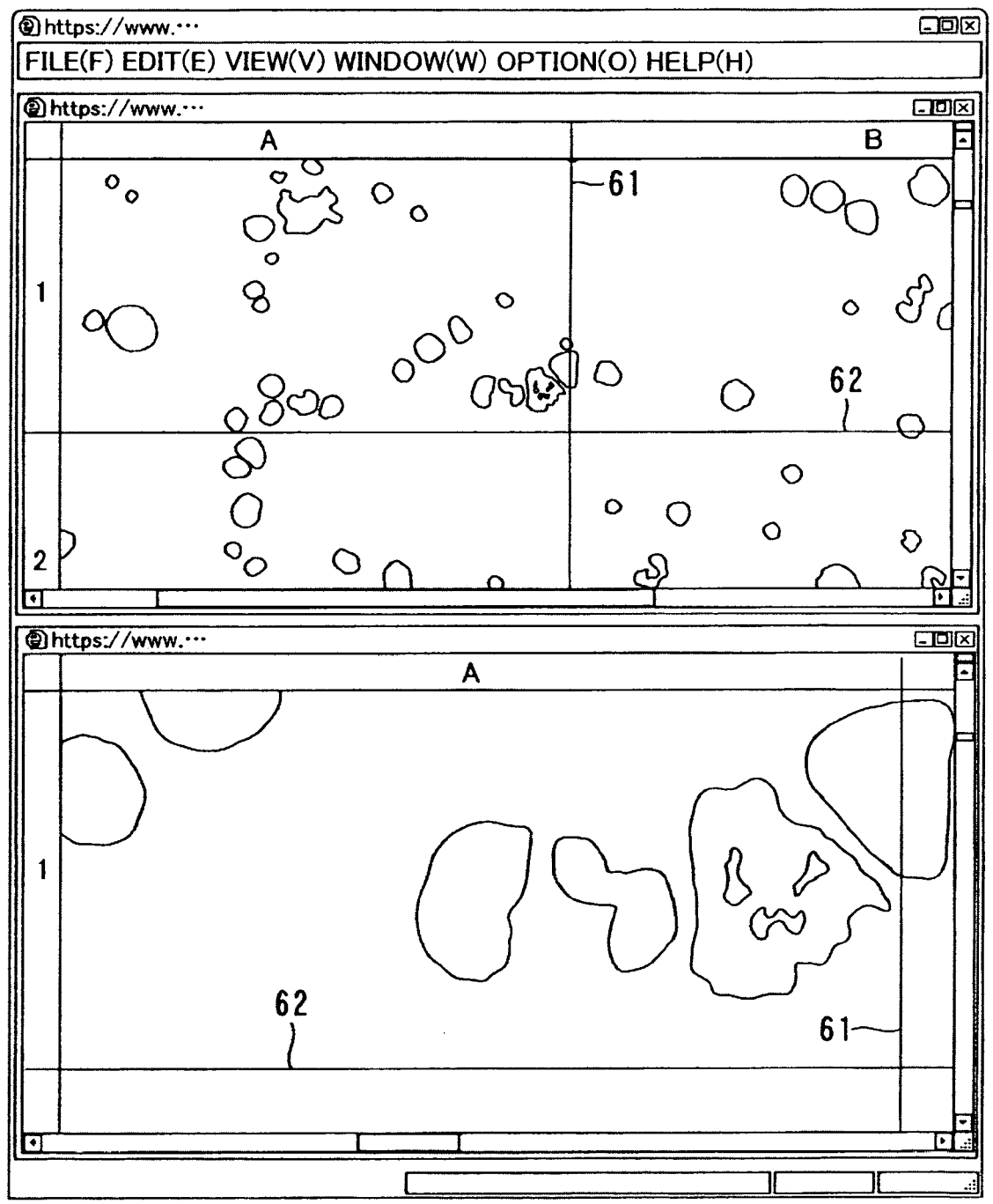
FIG. 9 shows an image display part according to an embodiment of the invention.

When the white blood cells are classified and counted at the client terminal 31, the image display function is activated at first in step S31 of the flow chart shown in FIG. 6. Specifically, an input screen for a user ID and password is displayed on the client terminal 31 as shown in FIG. 7 by clicking an icon (not shown) for activating the image display function on the screen of the client terminal 31. After inputting the user ID and password in this input screen, the image display function is activated by clicking "OK" using the mouse 31$a$. This permits a virtual slide selection screen as shown in FIG. 8 to be displayed on the client terminal 31 in step S32. The file name used on the virtual slide selection screen comprises, for example, examination date (six figures)-sample number (seven figures)-staining method (two or three alphabet letters). Subsequently, after selecting the file in which desired virtual slide data are stored on the virtual slide selection screen shown in FIG. 8 in step S33, "OPEN" is clicked using the mouse 31$a$. This permits an window of the image display part to be displayed as shown in FIG. 9 in step S34. In this case, a partial image of the selected virtual slide with a magnification of 20 (weak magnification) is scrollably displayed at the top of the image display part. A partial image of the virtual slide with a magnification of 100 (strong magnification) corresponding to the central portion of the virtual slide with a magnification of 20, which is displayed at the top of the image display part, is scrollably displayed at the bottom of the image display part.

The image data of the divided image 51 and low magnification image 52 necessary for displaying the partial image, of the divided image 51 with a magnification of 100 (see FIG. 4) and the low magnification image 52 with a magnification of 20 constituting the virtual slide, are preferentially delivered from the server 21 to the client terminal 31, when the partial image of the virtual slide is displayed on the client terminal 31. The remaining image data of the virtual slide are delivered as a background while the partial image 51 and low magnification image 52 thus delivered are displayed. In this case the divided image 51 and low magnification image 52 in a little wider area than the area displayed on the window of the image display part are preferentially received from the server 21 to the client terminal 31. This enables smooth scroll operations, since only partial images (divided image 51 and low magnification image 52) that have been acquired may be displayed without acquiring new partial images (divided image 51 and low magnification image 52) from the server 21 through the LAN cable 4, when the image is slightly scrolled while desired partial images (divided image 51 and low magnification image 52) are displayed.

The partial image of the virtual slide is displayed in step S34 by dynamically tiling a plurality of divided images 51 (low magnification images 52). Dynamic tiling refers to dynamically tiling respective images on the screen of the client terminal 31. The images have been already tiled when the virtual slide 50 (see FIG. 2) is prepared in this dynamic tiling, and the divided images 51 (low magnification images 52) are merely tiled again thereafter. Consequently, no shift between adjoining images occurs. Therefore, the tiling time may be shortened by dynamic tiling since no image recognition processing is necessary, different from image tiling for preparing the virtual slide in step S10 (see FIG. 3). In addition, since the divided image 51 (low magnification images 52) required for display of the partial image is preferentially downloaded to the client terminal 32, the time required for display is suppressed from being lengthened.

A default magnification of the partial image of the virtual slide displayed at the top and bottom of the image display part in step S34 shown in FIG. 6 may be arbitrarily selected from prescribed several kinds of magnifications. For example, the default value can be selected from magnifications of 10, 20, 40, 60 and 100. Since magnifications of 20 and 100 are selected as the default magnifications of the virtual slides displayed at the top and bottom of the image display part, respectively, in this embodiment, the virtual slide is displayed by dynamic tiling by receiving the low magnification image 52 with a magnification of 20 prepared in step S24 (see FIG. 5) and the divided image 51 with a magnification of 100 prepared in step S13. A weak magnification cell images with a magnification of 20 or 40 may be displayed at the bottom of the image display part in this embodiment, while a strong magnification image with a magnification of 100 is displayed at the top of the image display part.

The partial image of the virtual slide displayed in step S34 may be scrolled (transfer of the field of vision) in an arbitrary direction using the mouse 31a and the like. Whether or not the field of vision has been transferred out of the range of the imported image is judged in step S34. When judged to have been transferred out of the range of the imported image, the database 21a of the server 21 is accessed from the client terminal 31, and individual partial images (divided image 51 or low magnification image 52) corresponding to the field of vision that newly became required for display by scrolling are incorporated into the client terminal 31 from the server 21 through the LAN cable 4. The divided image 51 or low magnification image 52 in a little wider area than the area that is displayed on the screen is preferentially received from the server 21 to the client terminal 31. This enables the screen to be smoothly scrolled, since only the partial image (the divided image 51 or low magnification image 52) that have been acquired in the preceding scrolling may be displayed without acquisition of new partial images (the divided image 51 or low magnification image 52) from the server 21 through the LAN cable 4, when a small range of additional scrolling is necessary after preceding scrolling. The field of vision can be shifted during dynamic tiling.

Figure 10:
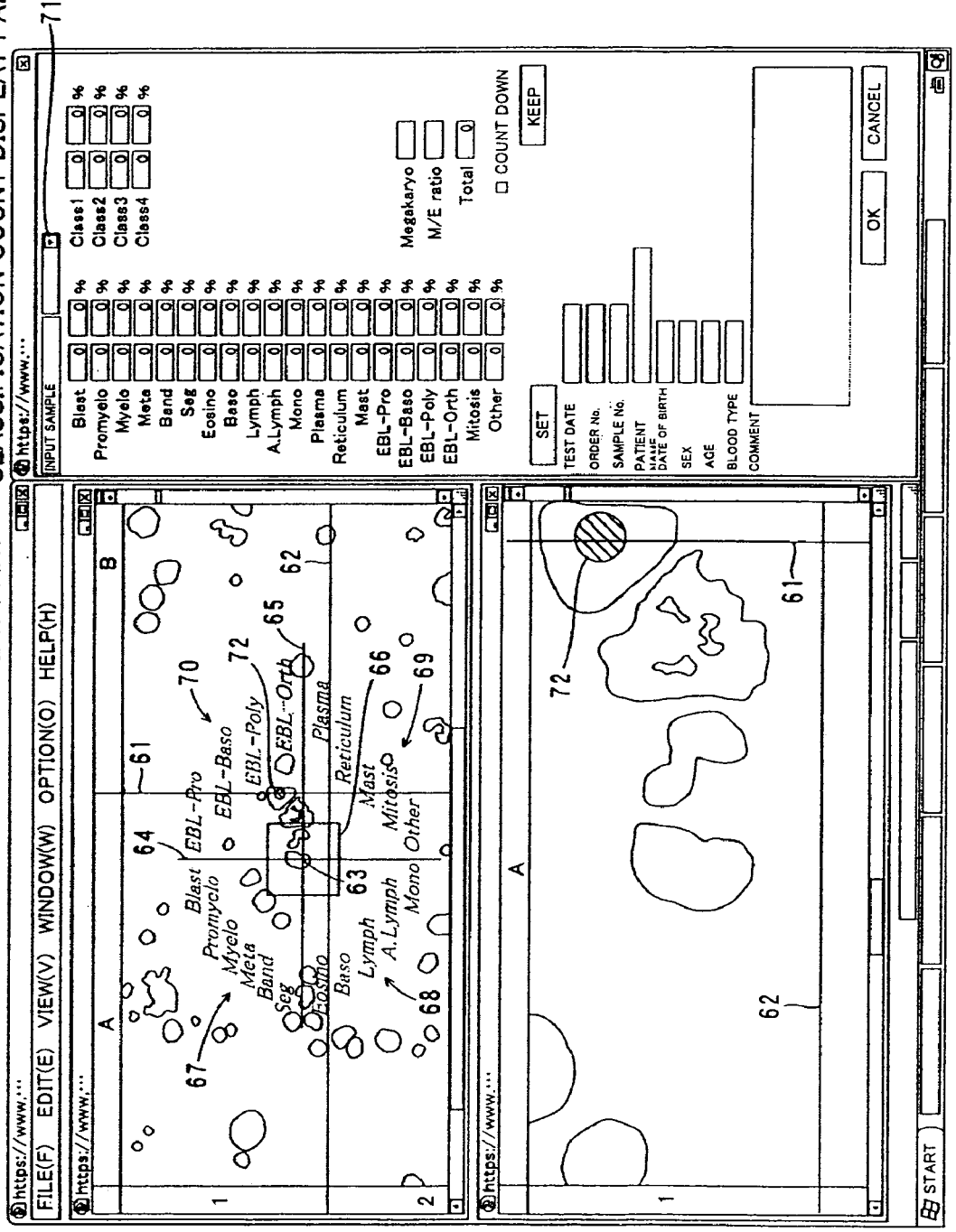
FIG. 10 shows a classification count screen including an image display part and a classification count display part according to an embodiment of the invention.

After displaying the partial image of the virtual slide in step S34 as is described above, it is judged whether the classification count function has been activated or not in step S35. When judged not, the classification count function is activated in step S36. The classification count function is activated, for example, by selecting a classification count menu from a pop-up function list by right-click of the mouse 31a. This permits the classification count display part to be displayed as a different window as shown in FIG. 10 at a position adjacent to the window of the image display part in FIG. 9. In this classification count display part, the count number and proportion (%) of 20 minor classes of the white blood cells, and the count number and proportion (%) of 4 major classes (classes 1 to 4) of the white blood cells are displayed.

Twenty minor classes of the white blood cells shown in FIG. 10 comprise, as shown in FIG. 12, Blast (blast cell), Promyelo (promyelocyte), Myelo (myelocyte), Meta (metamyelocyte), Band (band cell), Seg (segmented leukocyte), Eosino (eocinophile leukocyte), Baso (basocyte), Lymph (lymphocyte), A. Lymph (abnormal lymphocyte), Mono (monocyte), EBL-Pro (proerythroblast), EBL-Baso (basophilic erythroblast), EBL-Poly (polychromatic erythroblast), EBL-Orth (orthochromatic erythroblast), Plasma (plasma cell), Reticulum (reticular cell), Mast (mast cell), Mitosis (mitosis cell) and Other (other cells). The four major classes of the white blood cells, of the 20 minor classes described above, shown in FIG. 10 comprise: class 1 (bone marrow cells) to which Blast (blast cell), Promyelo (promyelocyte), Myelo (myelocyte), Meta (metamyelocyte), Band (band cell) and Seg (segmented leukocyte) belong; class 2 (white blood cells other than bone marrow cells) to which Eosino (eocinophile leukocyte), Baso (basocyte), Lymph (lymphocyte), A. Lymph (abnormal lymphocyte) and Mono (monocyte) belong; class 3 (erythroblasts) to which EBL-Pro (proerythroblast), EBL-Baso (basophilic erythroblast), EBL-Poly (polychromatic erythroblast) and EBL-Orth (orthochromatic erythroblast) belong; and class 4 (other white blood cells) to which Plasma (plasma cell), Reticulum (reticular cell), Mast (mast cell), Mitosis (mitosis cell) and Other (other cells) belong.

Since a clinical technologist or clinical examination physician considers the detailed minor classes in counting the blood cells (white blood cells) after judging to which major class the cell belongs, hierarchy of the major class and minor class shown in FIG. 12 is in accordance with the logical consideration of the clinical technologist or clinical examination physician in counting the cells.

A line of attribute information such as date of examination, request number, sample number, name of patient, date of birth, sex, age, blood type and comment on the sample acquired from the database 21a of the server 21 is displayed on the classification count display part. Input of attribute information is also possible at the clarification count display part. When attribute information is inputted, an input screen (not shown) is displayed as a different window by clicking an "SAMPLE ATTRIBUTE INPUT" button. By inputting attribute information at this input screen, the inputted attribute information is displayed on the classification count display part. Whether megakaryo cells are many (+) or few (−) may be inputted and displayed in the "megakaryo cell column" in the classification count display part. An M/E ratio indicating the ratio of M-cells and E-cells, and the total count number may be also displayed in the classification count display part. It is possible to determine to which major class the name of item of the minor class and the minor class itself belong by clicking "SETUP" button in the classification count display part.

The "SAVE" button and "OK" button in the classification count display part are used when the results of classification are stored in the client terminal 31. The "CANCEL" button is used when the results of classification are not stored in the client terminal 31. The "COUNT DOWN" check box is used when the results of classification are corrected (compiled).

After activating the classification count function described above, the virtual slide selected in step S32 is subjected to classification count in step S37. The classification count in step S37 is also implemented when the classification count function is judged to have been activated in step S35.

The classification count method using the virtual slide in step S37 will be described below in detail. The virtual slide with a magnification of 100 (strong magnification) displayed at the bottom of the image display part, and the virtual slide with a magnification of 20 (weak magnification) displayed at the top of the image display part shown in FIG. 10 are used in this embodiment for classification count. Positional base lines 61 and 62 as references of the position of cell images are displayed at the top and bottom of the image display part. Alphabet letters ("A" and "B") and figures ("1" and "2") that indicate the areas divided by the positional base lines 61 and 62 are displayed at the upper end and left-side end of the top and bottom of the image display part. Switching of display/non-display is possible with respect to the positional base lines 61 and 62.

Figure 11:
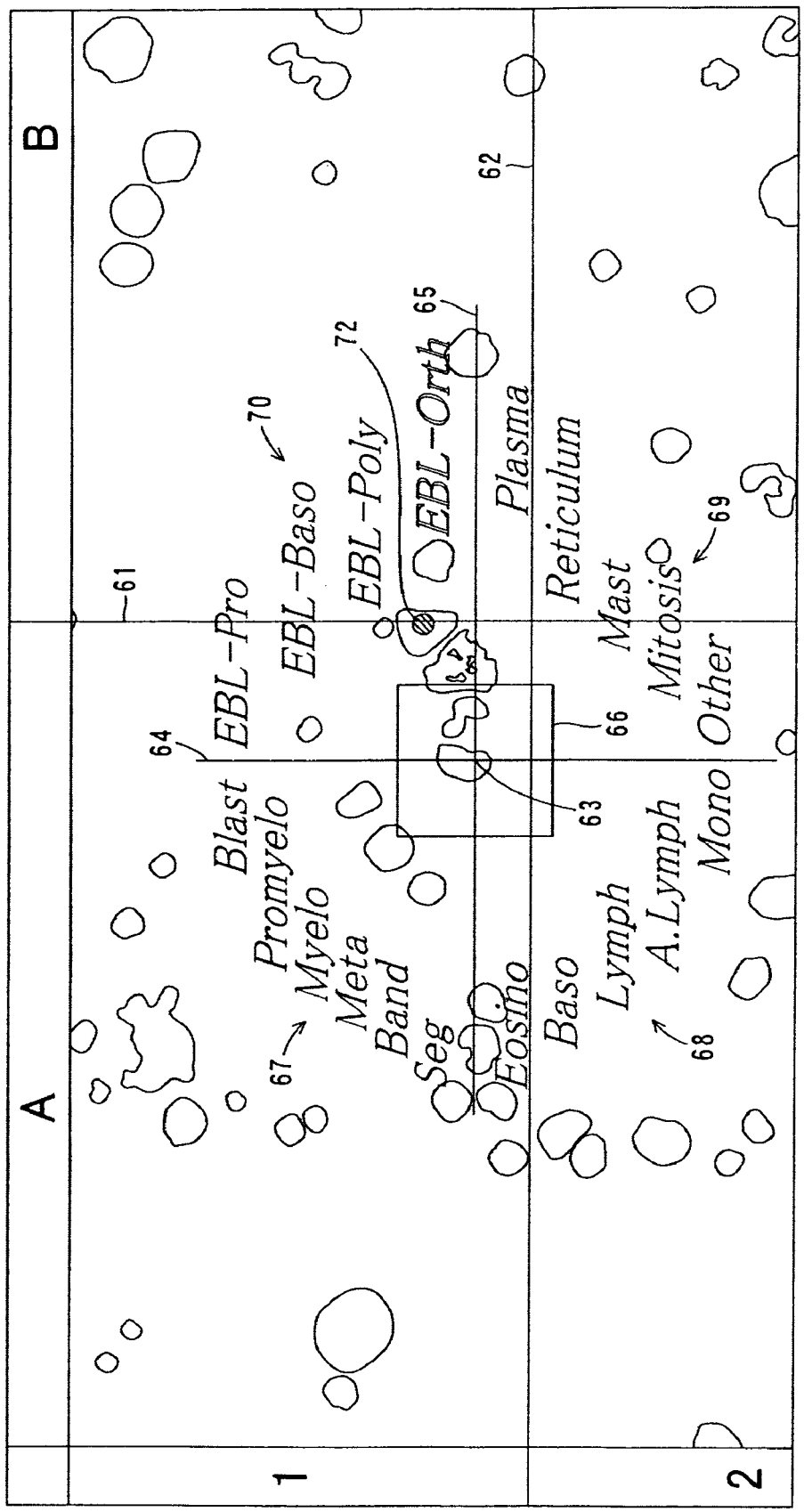
FIG. 11 is a partially magnified drawing at the top of the image display part shown in FIG. 10.

The mouse cursor points the position 63 of a cell (position of the specified cell) to be classified in the virtual slide displayed at the top of the image display part for classification count. When the left button of the mouse 31a is pushed at the position 63 of the specified cell while the mouse cursor is slightly displaced with the left button remain pushed, letters showing the classified cell name (minor class) of 20 classes of the white blood cell are displayed as, for example, black pop-up letters so as to surround the position 63 of the specified cell in an approximately circular shape centered at the position 63 as shown in FIGS. 10 and 11. These letters are displayed as images through which the background is visible so that the cell image at the display area of the letters can be visually recognized.

Major class division lines 64 and 65 are displayed so as to pass through the position 63 of the specified cell, wherein the lines divide four major classes [class 1 (bone marrow cells) 67, class 2 (white blood cells other than bone marrow cells) 68, class 3 (erythroblasts) 69 and class 4 (other white blood cells) 70] to which minor classes displayed in an approximately circular shape belong, and the lines are perpendicular to one another. A square boundary defining line 66, which defines a boundary between the minor class selection area and major class selection area centered at the position 63 of the specified cell, is also displayed in the virtual slide. This boundary defining line 66 is displayed in red color, for example, so as to be readily recognized by the naked eye.

When the major class and minor class are displayed, the mouse cursor is moved at a position corresponding to the letters indicating the classified cell name to be selected within the minor class selection area inside of the boundary defining line 66 while the left button of the mouse 31a remains pushed. Then, the selected cell name classified into the minor class [for example EBL-Orth (orthochromatic erythroblast)] turns from black into red, thereby enabling the minor class to be selected. When the judgment to which minor class the cell belongs is difficult, the mouse cursor is moved to the major class division area selected in the major class selection area outside of the boundary defining line 66 with the left button of the mouse 31a remain pushed while the major classes 67 to 70 and minor classes are displayed. Then, all the classified cell names in the minor class belonging to the selected major class turn from black to red, permitting the major class to be selected. The minor class or major class is selected as described above. When the left button of the mouse 31a is released thereafter, the cell number in the selected minor class or major class is counted, and the total count number is displayed in the item corresponding to the minor class or major class selected in the classification count display part in FIG. 10. The results of classification count including count number, cell image of the counted cell, positional information, classification name, classification date and name of the person in charge of classification are stored in the client terminal 31 while counting. The cell image is stored as a full color image with a resolution of 80 dots×80 dots in the JPEG format, and the positional information is stored as an (X, Y) position on the virtual slide.

Since the classification count as well as storing of the cell image and positional information of the counted cell in the client terminal 31 are executed at the same time in this embodiment, it is possible to readily retrieve (search) the cell image based on the stored positional information. The minor class is selected by displaying the pop-up menu including the 20 minor classes of the white blood cell by handling the button of the mouse 31a at the image display part of the client terminal 31 on which the virtual slide is scrollably displayed, and the count number corresponding to the selected minor class is displayed at the classification count display part as is described above. Accordingly, operationability is improved because scroll action of the virtual slide as well as classification count work such as selection of the minor class are possible using the mouse 31a. This enables the classification count work using the virtual slide to be efficiently performed. Operationability is further improved by effecting the classification count work by one click of the mouse 31a.

The sound for storing may be different among the four major classes, when the selected major class is stored. Since visual as well as auditory recognition of the stored major class is possible, incorrect selection may be recognized by auditory sense even when incorrect selection of the major class is not visually noticed, thereby enabling incorrect selection to be reduced in classification count.

A mark (to be described below) indicating the cells after classification count is displayed in red color on the cell image with stored classification count. Classification count for one cell in step 37 is thus completed.

Subsequently, whether classification count of the prescribed count number has been completed or not is judged for the selected virtual slide in step S38. The classification count action in step S37 is repeated when judged not. The classification count number is set to be about 100 counts for the peripheral blood, while the number is set to be 500 to 1000 counts for the bone marrow blood. This count number is set by selecting a plurality of count numbers displayed by clicking a tub 71 of pull-down menus of the classification count display part shown in FIG. 10. When classification count with a prescribed count number is judged to have been completed for the selected virtual slide in step S38, whether other samples (virtual slides) are to be classified or not is judged in step S39.

When other samples (other virtual slides) are judged to be classified in step S39, the operations from step S33 through step S38 are repeated. Actually, a menu list is displayed on the screen by clicking "FILE (F)" of a menu bar at the top of the screen shown in FIG. 10 with the mouse 31a, when other samples are judged to be classified. The virtual slide selection screen shown in FIG. 8 is displayed by clicking "OPEN (O)" menu in the menu list with the mouse 31a. Classification count is implemented for other samples by repeating the operations from the above-described step S33 through step S38 from the state described above.

When other samples are judged not to be classified in step S39, the results of classification count in step S37 are uploaded to the server 21 (see FIG. 1) in step S40, and the data are registered in the database 21a. Actually, the menu list is displayed on the screen by clicking "FILE (F)" in the menu bar at the top of the screen shown in FIG. 10 with the mouse 31a. The results of classification count that have been stored in the client terminal 31 are registered in the server 21 (see FIG. 1) by clicking the "FINAL REGISTRATION (O)" in the menu list with the mouse 31a.

Figure 14:
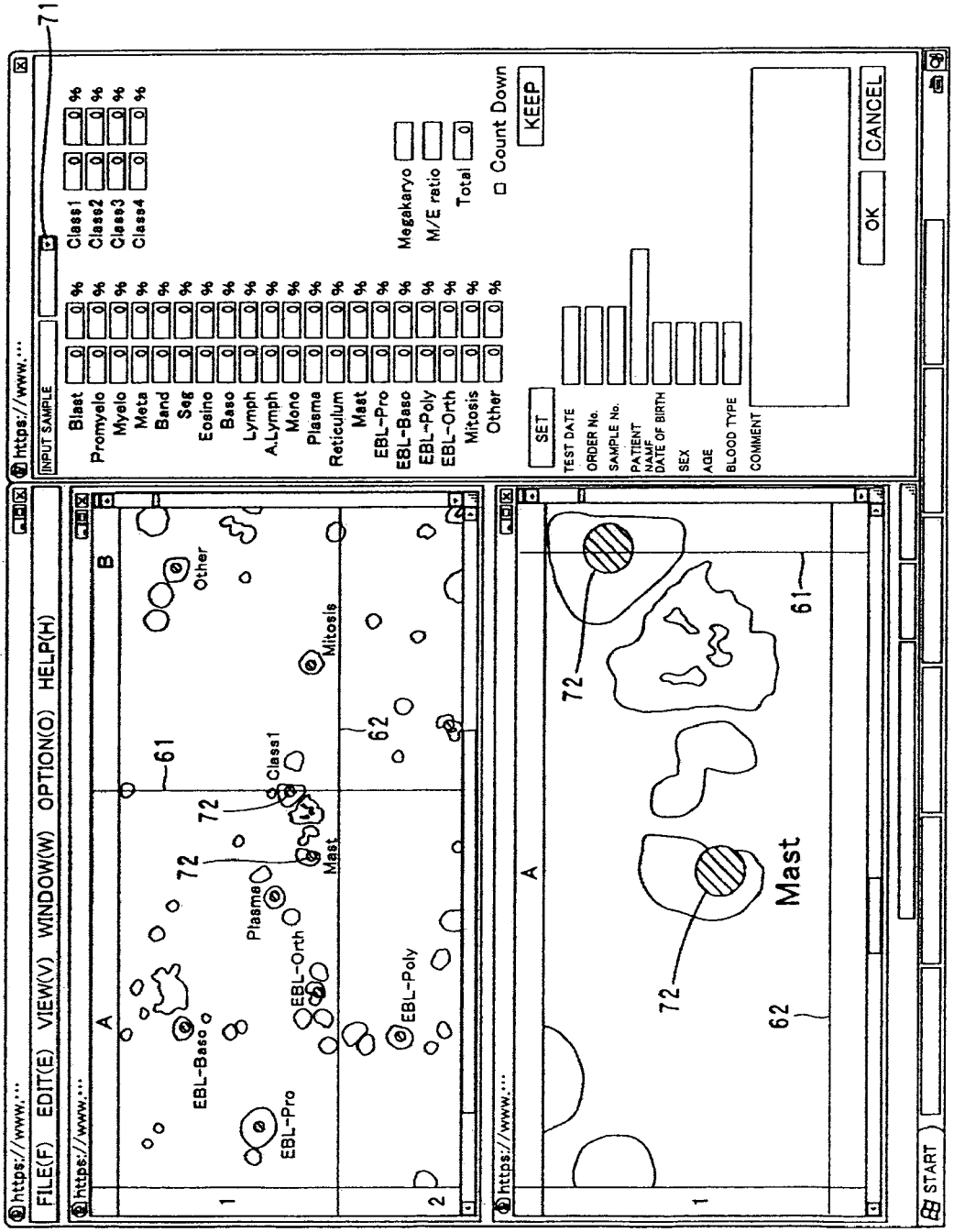
FIG. 14 shows a classification name display screen in the action for confirming the results of classification according to an embodiment of the invention.
Figures 15, 16:
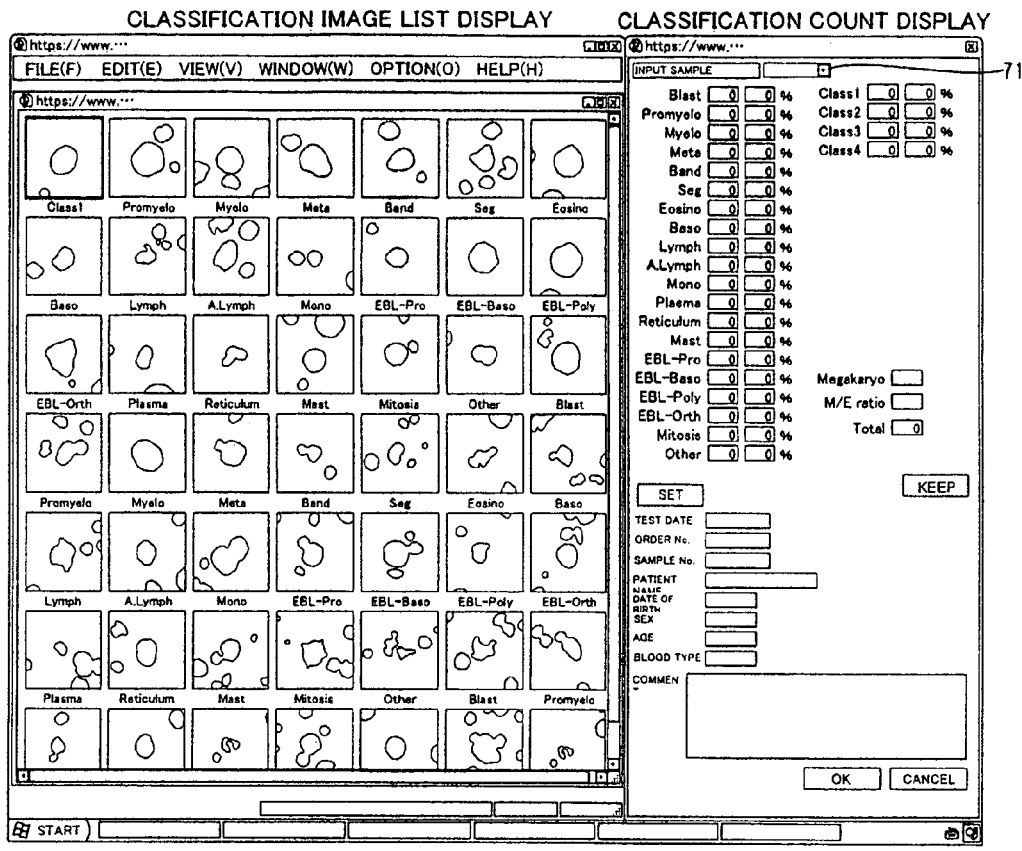
FIG. 15 shows a classified image reference screen in the confirmation action of the results of classification according to an embodiment of the invention.
FIG. 16 shows a flow chart for describing compilation action of the results of classification according to an embodiment of the invention.

FIG. 13 shows a flow chart for illustrating a confirmation action (re-judgment action) of the result of classification, while FIG. 14 shows a classification name display screen as an example of the screen displayed for confirming the results of classification. FIG. 15 shows a classified image reference screen (thumbnail screen) as another example of the screen displayed for confirming the results of classification. The confirmation action (re-judgment action) will be described below with reference to FIGS. 13 to 15. For confirming classification count, the operations shown in steps S41 to S44 in the flow chart shown in FIG. 13 are executed first. Steps S41 to S44 are the same as steps S21 to S24 of the classification count action shown in FIG. 6. The image display function is activated at first by clicking "OK" after input of a user ID and password in the input screen (see FIG. 7) for inputting the user ID and password displayed in the client terminal 31 in step S41. This permits the virtual slide selection screen (see FIG. 8) to be displayed in step S42. Then the virtual slide for confirming (re-judging) the results of classification count is selected on the virtual slide selection screen in step S43, and "OPEN" is clicked. Consequently, the partial images with magnifications of 20 and 100, respectively, of the selected virtual slide are scrollably displayed in step S44 at the top and bottom of the window of the image display part as shown in FIG. 9.

Subsequently, the method for confirming the results of classification count is selected in step S45. Actually, the method for confirming the results of classification is selected from "NUMERAL FORMAT", "CLASSIFICATION NAME DISPLAY FORMAT" or "CLASSIFIED IMAGE REFERENCE FORMAT" displayed in the menu list according to a prescribed operation mode. When "NUMERAL FORMAT" is selected in step S45, the classification count function is activated in step S46. Actually, the classification count display part is displayed as a different window as shown in FIG. 10 at a position adjacent to the window of the image display part in FIG. 9, by selecting the classification count menu from the function list displayed as a pop-up image by right-click of the mouse 31a. The results of classification count are confirmed in the numeral format in the classification count display part in step S47.

When "CLASSIFICATION NAME DISPLAY FORMAT" is selected in step S45, the classification name display screen is activated as shown in FIG. 14 in step S48. In this classification name display screen, the classification name display part and the classification count display part are displayed. A similar cell image as that in the image display part shown in FIG. 10 is displayed in the classification name display part shown in FIG. 14 while the classification name in the minor class or major class is displayed in the vicinity of each cell image that has been subjected to classification count. Consequently, the cell image may be re-judged by observing the cell image, classification name counted for the cell image and the images around the cell image. A red circular mark 72 as a discrimination mark showing the cell after classification count is displayed at each cell image. Switching of display/non-display is possible for the classification name of the classification name display part and circular mark 72. The results of classification count are confirmed or re-judged based on the cell image displayed in the classification name display part and classification name corresponding to the cell image in step S50. It is also judged whether classification count is to be corrected (compiled) or not in step S51.

When it is judged to compile (correct) classification count in step S51, the step advances to the classification result compilation flow (step S61 in FIG. 16) from step S52. The results of classification are corrected in step S61 in FIG. 16. Actually, the red circular mark 72 of the cell image to be corrected is clicked with "COUNT DOWN" in the classification count display part (see FIG. 14) being checked by pointing "COUNT DOWN" with the mouse cursor, thereby deleting the results of classification count of the cell image. Subsequently, the check is released by pointing "COUNT DOWN" with the mouse cursor. Classification count of the cell image to be corrected is resumed by the same method as in classification count shown in FIG. 10, and whether correction of the classification results has been completed or not is judged in step S62. When judged to have been completed, the corrected results of classification count are uploaded to the server 21 (see FIG. 1) in step S63 by the same method as in step S30 (see FIG. 6) followed by registering in the database 21a. Compilation of the results of classification in the classification name display screen is then completed.

When the results of classification are judged not to be compiled in step S51 in FIG. 13, whether the results of other classification count are to be confirmed or not is judged in step S53. When the results of other classification count are judged not to be confirmed in step S53, compilation is immediately completed. On the other hand, when judged to be confirmed, operations in step S43 and thereafter are continued.

When "CLASSIFIED IMAGE REFERENCE FORMAT" is selected in step S45, the classified image reference screen (thumbnail screen) as shown in FIG. 15 is activated in step S49. A classified image list display part (thumbnail display part) and classification count display part are displayed in this classified image reference screen. The list of the each cell image subjected to classification count as well as the classification name of the minor class or major class for each cell image are displayed in the classified image list display part. This permits the cell image to be judged (confirmed) again to be readily retrieved from the cell images in the list. Then, the results of classification count are confirmed or re-judged by the classified image list display part in step S50. The classification name display part in FIG. 14 is displayed in place of the classified image list display part in FIG. 15 by clicking the cell image to be re-judged in the list, and the cell corresponding to the clicked cell image is displayed at the center of the virtual slide of the classification name display part based on positional information of the stored cell itself. Since the sample images containing the cell image to be re-judged and cell image in the vicinity of the cell image to be re-judged are displayed, the cell image may be readily re-judged. Whether the classification count is to be corrected (compiled) or not is judged in step S51.

When it is judged to compile (correct) classification count in step S51, the step advances to the compilation flow (S61 in FIG. 16) of the results of classification in step S52. When the results of classification are corrected in the classified image list display part (thumbnail display part), the thumbnail image to be corrected is selected, and classification count of the cell image is deleted by selecting a displayed delete menu by pressing the right button of the mouse 31a. Then, the cell image to be corrected is subjected to classification count again by handling the mouse by the same method as in classification count shown in FIG. 10. Specifically, this step comprises pointing the mouse cursor at the position of the cell to be classified in the thumbnail image, slightly moving the mouse cursor with the left button of the mouse remain pressed, displaying the letters indicating the classified cell name (minor class), and selecting the classified cell name (minor class) by further moving the mouse cursor in the minor class selection area. Numerical values are counted for the item corresponding to the selected minor class in the classification count display part in FIG. 15 by releasing the left button of the mouse, and the results of classification count such as the cell image of the counted cell, positional information, classification name, classification date and name of the person in charge of classification are stored in the client terminal 31. When re-judgment is difficult using only the thumbnail image, the cursor is moved to the position of the cell on the virtual slide by clicking the thumbnail image to be corrected, and the cell image to be corrected is subjected to classification counting again by the same mouse operation as in the classification count method shown in FIG. 10. Whether correction of the results of classification has been completed or not is judged thereafter in step S62. When judged to have been completed, the results of classification count after correction are uploaded in the server 21 (see FIG. 1) in step S63 by the same method as in step S30 (see FIG. 6), and are registered in the database 21a. Compilation of the results of classification in the classified image list display part is thus completed.

The action is the same as that in the classification name display screen described above, when the results of classification are judged not to be compiled in step S51.

An example of the operation network of the virtual slide data will be described below with reference to FIG. 17. In the operation network shown in FIG. 17, the server 21 including the database 21a in which the virtual slide and the results of classification count are stored is connected to each client terminal 31 for the clinical technologists, clinical examination physician and clinical physician through LAN, internet or exclusive line (not shown). The network is constructed so that the clinical technologists, clinical examination physician and clinical physician are able to inspect the virtual slide and the results of classification count stored in the database 21a of the server 21 on each of their client terminals 31. Consequently, the clinical technologist, clinical examination physician and clinical physician are able to exchange a line of information through the network.

Figure 17:
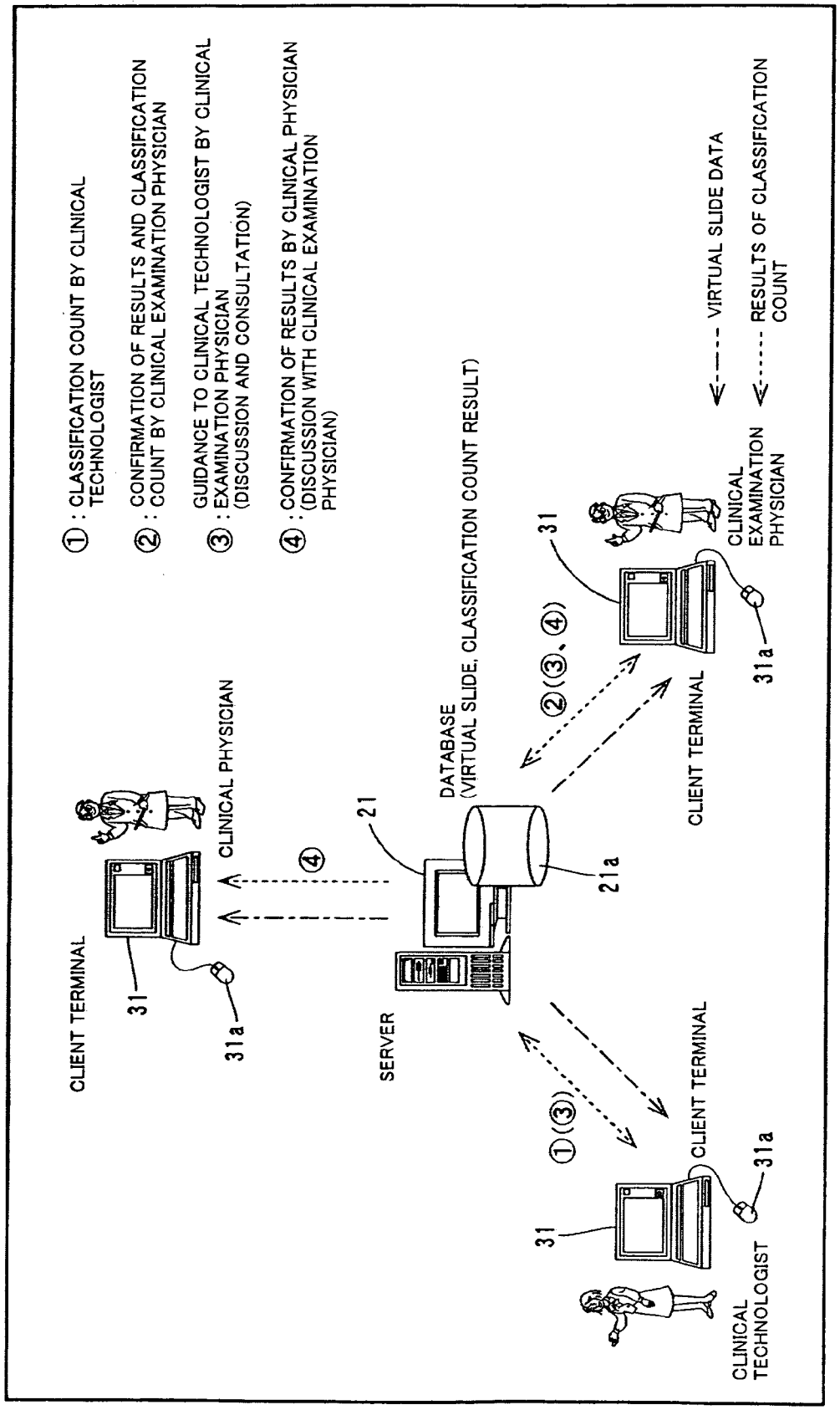
FIG. 17 is provided for illustrating an example of an operation network of virtual slide data according to an embodiment of the invention.

In a typical flow of operation shown in FIG. 17, the virtual slide to be subjected to classification count is incorporated into the client terminal 31 of the clinical technologist from the database 21a of the server 21, or the virtual slide is delivered real-time to the client terminal 31 from the server 21. The clinical technologist classifies and counts the sample using the virtual slide displayed on the client terminal 31 having the mouse 31a. The clinical technologist also corrects (compiles) the results of classification count, if necessary. Then, the clinical technologist stores the results of classification count in the database 21a of the server 21 through the network. On the other hand, the clinical examination physician confirms and re-judges the results of classification count stored in the database 21a of the server 21 after importing them into the client terminal 31, and corrects (compiles) the results of classification count, if necessary. When the results of classification count are corrected, the clinical examination physician uploads the corrected results of classification count to the database 21a of the server 21. The clinical technologist consults with the clinical examination physician about the results of classification count (consultation) through the network, and the clinical examination physician guides the clinical technologist. Consultation and guidance are performed while the classification name display screen shown in FIG. 14 is displayed on respective client terminals 31 of the clinical technologist and clinical examination physician. Since the positional base lines 61 and 62 (see FIG. 14) as references of the position of the cell image, and letters (alphabet letters and numerals) indicating the area divided by the positional base lines 61 and 62 are displayed on the classification name display part on the classification name display screen, the position of the cell can be readily located using the positional base lines 61 and 62 and letters indicating the divided area. Accordingly, consultation and guidance become smooth between the clinical examination physician and clinical technologist.

After confirming or compiling the results of classification count by the clinical examination physician, the clinical physician confirms the results of classification count by importing them into his or her client terminal 31 from the database 21a of the server 21 through the network. The clinical physician and the clinical examination physician exchange their opinion on the results of classification count through the network. The position of the cell can be readily located in this discussion between the clinical physician and the clinical examination physician by displaying the positional base lines 61 and 62, and the classification name display screen including the letters indicating the divided area. Accordingly, the clinical physician is able to smoothly discuss with the clinical examination physician.

As described above, the virtual slide photographed with a magnification capable of recognition of the cell morphology is scrollably displayed on the client terminal 31 in this embodiment. In addition, the cell image can be readily retrieved based on positional information by storing at least positional information of the specified cell in the virtual slide during classification count. Consequently, re-judgment of the cell image is facilitated.

In this embodiment, the cell image and positional information of the classified cell can be readily stored by executing classification count and storing of the cell image and positional information of the classified cell at the same time.

In this embodiment, a partial image (divided image 51 or low magnification image 52) necessary for display on the client terminal 31, of the partial images (divided image 51 or low magnification image 52) stored in the database 21a of the server 21, is preferentially acquired from the server 21 through the LAN cable 4 and displayed as is described above. Consequently, a large size of the image data is not required to be received at once for displaying on the client terminal 31. Instead, the image data of the partial image (divided image 51 or low magnification image 52) necessary for display may be preferentially received to enable prolongation of the time required for display to be suppressed, and to enable communication stress to be reduced. When the partial image that became required for display in accordance with scroll action in the client terminal 31 has not been delivered to the client terminal 31, the required partial image is preferentially acquired from the server 21 through the LAN cable 4 and displayed. Consequently, a large size of image data is not required to be received at once for display in the scroll action. Instead, the image data of the partial image (divided image 51 or low magnification image 52) necessary for display may be preferentially received to enable delay of the scroll action caused by prolonged time necessary for display to be suppressed.

The embodiment disclosed herein is only examples in all aspects, and should be considered not to be restrictive. The scope of the invention is not described in the embodiment set forth above, but is indicated in the claims. All modifications are included within equivalence and scope of the claims.

While the invention has been described in examples for applying the method for displaying the blood cell image in this embodiment, the invention is not restricted thereto, and is applicable to the method for displaying sample images other than the blood cell images.

While positional information of the cell and cell images are stored using the mouse as an example of a pointing device in the embodiment, the invention is not restricted thereto, and other pointing devices may be used for storing positional information of the cell and cell images. Examples of other pointing devices include a track ball for moving the cursor by rotating a ball exposed on the operation board with the hand, a track pad for moving the cursor by tracing on a flat plastic plate with a finger, and a tablet for moving the cursor by displacing a small instruction device such as a pen on a exclusive use table.

While classification of the blood cell is selected using the mouse in classification count according to the embodiment, the invention is not restricted thereto, and classification of the blood cell may be selected using the key board and mouse together. For example, a minor class belonging to a major class may be displayed as a pop-up menu at the position of the mouse cursor after selecting the major class with the key board, and the minor class may be selected from the pop-up menu by mouse operation.

In the embodiment, letters indicating the classified cell name (minor class) are displayed so as to surround the position pointed by the left button by slightly moving the mouse cursor while the left button of the mouse remains pressed after pointing the cell with the mouse cursor during classification count. However, the invention is not restricted thereto. The letters indicating the classified cell name (minor class) may be displayed by merely pressing the left button of the mouse so as to surround the pressed position after pointing the cell with the mouse cursor. This enables operationability of the classification count action to be more improved. When the letters indicating the classified cell name (minor class) are displayed so as to surround the position where the left button of the mouse is pressed, they may be displayed so as to surround the position by, for example, a square in place of a circle.

In the embodiment above, the minor class or major class is selected by moving the mouse cursor to the position corresponding to the selected class in classification count while the left button of the mouse remains pressed, and the results of classification are counted thereafter by releasing the left button of the mouse. However, the invention is not restricted thereto, and the same results of classification as those in the preceding step may be counted, or the same results of classification as those in the preceding step may be displayed merely by clicking the mouse. Since the classification count work of the cell belonging to the same class as that of the cell counted in the preceding step may be more simplified, the classification count work using the virtual slide may be more efficiently performed.

While classification count of the white blood cell has been described in the embodiment above, the invention is not restricted thereto, and the same process may be applied for classification count of blood cells other than the white blood cell.

While the network is constructed as shown in FIG. 1 by connecting the automatic stage control terminal, the server and client terminal to the LAN cable in the example shown in FIG. 1, the invention is not restricted thereto, and an internet line or an exclusive use line may be used in place of the LAN cable.

While the virtual slide prepared is stored in the server after focus synthesis and image tiling in the automatic stage control terminal in the embodiment above, the invention is not restricted thereto, and the focus synthesis image may be stored in the server after focus synthesis in the automatic stage control terminal to prepare the virtual slide by image tiling in the server.

What is claimed is:

1. A method for displaying a virtual slide comprising steps of:
   providing a plurality of divided images prepared by dividing the virtual slide photographed with a magnification capable of recognizing blood cells morphology, wherein the virtual slide is obtained by image tiling a plurality of focus-synthesized images in a different field of vision and each of the focus-synthesized images is obtained by synthesizing a plurality of focused images having different focuses in a same field of vision;
   displaying an image display part for displaying the virtual slide by dynamically tiling the divided images and a pointer for specifying a blood cell displayed on the image display part;
   receiving a specification instruction for specifying a white blood cell in the blood cells by the pointer;
   receiving a classification instruction for classifying the specified white blood cell into subclasses, and
   storing positional information of the classified white blood cell, the classified subclass and an image of the classified white blood cell in a memory based on the classification instruction.

2. The method according to claim 1, further comprising the step of displaying a list of a plurality of stored white blood cell images.

3. The method according to claim 2, further comprising a step of displaying the virtual slide on the image display part by selecting the specified white blood cell image from the plural white blood cell images in the list so that the selected white blood cell image is displayed in the displayed virtual slide based on the stored positional information of the selected white blood cell.

4. The method according to claim 1, wherein the displaying step is performed by displaying a classification count display part with the image display part, wherein the classification count display part displays count numbers for the every subclasses.

5. A terminal device for displaying a virtual slide comprising:
- a display;
- a memory storing a plurality of divided images prepared by dividing the virtual slide photographed with a magnification capable of recognizing blood cells morphology, wherein the virtual slide is obtained by image tiling a plurality of focus-synthesized images in a different field of vision and each of the focus-synthesized images is obtained by synthesizing a plurality of focused images having different focuses in a same field of vision; and
- a controller performs operations comprising: displaying a virtual slide on the display by dynamically tiling the divided images;
- a specification instruction for specifying a white blood cell in the virtual slide;
- receiving a classification instruction for classifying the specified white blood cell into subclasses; and
- storing positional information of the classified blood cells, the classified subclass and an image of the classified white blood cell in the memory.

6. The terminal device according to claim 4, comprising a pointing device in which movement of a pointer on the display is linked to movement of the pointing device but not to a position of the device,
wherein the displaying operation is performed by displaying the pointer on the displayed virtual slide.

7. The terminal device according to claim 5, comprising displaying a list of a plurality of the stored white blood cell images on the display.

8. The terminal device according to claim 7, comprising receiving an image selection instruction for selecting a prescribed white blood cell image from the list of the plural white blood cell images, and displaying the virtual slide on the display so that the selected white blood cell is displayed in the displayed virtual slide based on the stored positional information of the selected white blood cell.

9. The terminal device according to claim 5, comprising acquiring the virtual slide from a database storing the virtual slide through a communication network, and in the memory.

10. The terminal device according to claim 5, wherein the displaying operation is performed by displaying positional base lines and letters indicating an area divided by the positional base lines on the displayed virtual slide.

11. A method for displaying a virtual slide comparing: providing a plurality of divided images prepared by diving the virtual slide photographed with a magnification capable of recognizing blood cells morphology, wherein the virtual slide is obtained by image tiling a plurality of focus-synthesized images in a different field of vision and each of the focus-synthesized images is obtained by synthesizing a plurality of focused images having different focuses in a same field of vision; displaying an image in real-time on a remote display part that displays the virtual slide recorded with a remote magnification capable of recognizing blood cells morphology on a display and a pointer for specifying a blood cell displayed on the image display part; receiving a specification instruction for specifying a white blood cell through the pointer; receiving a classification instruction for classifying the specified white blood cell into subclasses; and storing positional information of the classified white blood cell, the classified subclass and an image of the classified white blood cell in a database machine based on the classification instruction; where the positional information is physically organized in the database machine with a table correlating a physical line of discrimination information and a plurality of attribute information unrelated to the line of discrimination and positional information.

12. The method according to claim 1, where the positional information is physically organized in a database machine with a table correlating a physical line of discrimination information.

* * * * *